(12) United States Patent
Cong et al.

(10) Patent No.: US 9,924,904 B2
(45) Date of Patent: Mar. 27, 2018

(54) POWER-EFFICIENT CHOPPER AMPLIFIER

(71) Applicant: Medtronic, Inc., Minneapolis, MN (US)

(72) Inventors: Peng Cong, Plymouth, MN (US); Michael B. Terry, Camas, WA (US)

(73) Assignee: Medtronic, Inc., Minneapolis, MN (US)

( * ) Notice: Subject to any disclaimer, the term of this patent is extended or adjusted under 35 U.S.C. 154(b) by 690 days.

(21) Appl. No.: 14/474,858

(22) Filed: Sep. 2, 2014

(65) Prior Publication Data
US 2016/0065133 A1 Mar. 3, 2016

(51) Int. Cl.
*H03F 1/02* (2006.01)
*A61B 5/00* (2006.01)
(Continued)

(52) U.S. Cl.
CPC .......... *A61B 5/6847* (2013.01); *A61B 5/0476* (2013.01); *A61B 5/4836* (2013.01);
(Continued)

(58) Field of Classification Search
CPC ... H03F 3/38; H03F 1/02; H03F 3/387; H03F 3/45475; H03F 3/45977; H03F 2200/333; H03F 2200/411; H03F 1/0205; H03F 3/45179; H03F 1/303; H03F 2003/45008; H03F 2200/231; H03F 2203/45112;
(Continued)

(56) References Cited

U.S. PATENT DOCUMENTS 1,342,885 A 6/1920 Armstrong
3,130,373 A 4/1964 Braymer
(Continued)

FOREIGN PATENT DOCUMENTS

CN 101099670 A 1/2008
EP 354060 A2 2/1990
(Continued)

OTHER PUBLICATIONS

"baseband." Academic Press Dictionary of Science and Technology. Oxford: Elsevier Science & Technology, 1992.
(Continued)

*Primary Examiner* — Khanh V Nguyen
(74) *Attorney, Agent, or Firm* — Shumaker & Sieffert, P.A.

(57) ABSTRACT

In an example, an electrical circuit device for amplifying a physiological signal includes a modulation unit configured to receive an input signal, to modulate the input signal to produce a modulated signal. The device also includes an amplification and transconductance unit configured to amplify an amplitude of the modulated signal and increase a transconductance of the modulated signal to produce a transconductance enhanced modulated and amplified signal, where the amplification and transconductance unit comprises at least a first complementary pair of transistors and a second complementary pair of transistors configured to receive the modulated signal and to amplify and increase the transconductance of the modulated signal. The device also includes a demodulation unit configured to receive the transconductance enhanced modulated and amplified signal and to demodulate the signal.

20 Claims, 5 Drawing Sheets

(51) Int. Cl.
*A61B 5/0476* (2006.01)
*H03F 3/393* (2006.01)
*H03F 3/45* (2006.01)
*H03F 3/217* (2006.01)
*H03F 1/30* (2006.01)
*A61N 1/36* (2006.01)
*A61N 1/365* (2006.01)

(52) U.S. Cl.
CPC ............ *A61B 5/686* (2013.01); *A61B 5/6868* (2013.01); *A61B 5/7228* (2013.01); *H03F 3/393* (2013.01); *H03F 3/4565* (2013.01); *H03F 3/45192* (2013.01); *H03F 3/45237* (2013.01); *H03F 3/45475* (2013.01); *A61N 1/36125* (2013.01); *A61N 1/36507* (2013.01); *H03F 1/303* (2013.01); *H03F 3/2178* (2013.01); *H03F 2200/171* (2013.01); *H03F 2200/231* (2013.01); *H03F 2200/261* (2013.01); *H03F 2203/45138* (2013.01); *H03F 2203/45424* (2013.01)

(58) Field of Classification Search
CPC .. H03F 3/393; H03F 3/45192; H03F 3/45237; H03F 3/4565; H03F 3/45076; A61B 5/6847; A61B 5/0476; A61B 5/4836; A61B 5/686; A61B 5/6868; A61B 5/7228
USPC ............................................................ 330/9
See application file for complete search history.

(56) References Cited

U.S. PATENT DOCUMENTS

| | | |
|---|---|---|
| 3,603,997 A | 9/1971 | Brouwer |
| 3,735,274 A | 5/1973 | Nelson |
| 3,780,725 A | 12/1973 | Goldberg |
| 4,138,649 A | 2/1979 | Schaffer |
| 4,177,819 A | 12/1979 | Kofsky et al. |
| 4,188,586 A | 2/1980 | Egami |
| 4,279,258 A | 7/1981 | John |
| 4,579,125 A | 4/1986 | Strobl et al. |
| 4,610,259 A | 9/1986 | Cohen et al. |
| 4,612,934 A | 9/1986 | Borkan |
| 4,733,667 A | 3/1988 | Olive et al. |
| 4,810,960 A | 3/1989 | Owen et al. |
| 4,933,642 A | 6/1990 | Lee |
| 4,979,230 A | 12/1990 | Marz |
| 5,024,221 A | 6/1991 | Morgan |
| 5,061,593 A | 10/1991 | Yoerger et al. |
| 5,105,167 A | 4/1992 | Peczalski |
| 5,113,143 A | 5/1992 | Wei |
| 5,179,947 A | 1/1993 | Meyerson et al. |
| 5,205,285 A | 4/1993 | Baker, Jr. |
| 5,206,602 A | 4/1993 | Baumgartner et al. |
| 5,282,840 A | 2/1994 | Hudrlik |
| 5,299,569 A | 4/1994 | Wernicke et al. |
| 5,311,876 A | 5/1994 | Olsen et al. |
| 5,334,222 A | 8/1994 | Salo et al. |
| 5,337,230 A | 8/1994 | Baumgartner et al. |
| 5,458,117 A | 10/1995 | Chamoun et al. |
| 5,477,481 A | 12/1995 | Kerth |
| 5,619,536 A | 4/1997 | Gourgue |
| 5,663,680 A | 9/1997 | Nordeng |
| 5,725,558 A | 3/1998 | Warnke |
| 5,777,235 A | 7/1998 | Altwein |
| 5,782,884 A | 7/1998 | Stotts et al. |
| 5,843,139 A | 12/1998 | Goedeke et al. |
| 5,928,272 A | 7/1999 | Adkins et al. |
| 6,006,163 A | 12/1999 | Lichtenwalner et al. |
| 6,011,990 A | 1/2000 | Schultz et al. |
| 6,016,444 A | 1/2000 | John |
| 6,018,682 A | 1/2000 | Rise |
| 6,061,593 A | 5/2000 | Fischell et al. |
| 6,064,257 A | 5/2000 | Sauer |
| 6,070,101 A | 5/2000 | Struble et al. |
| 6,129,681 A | 10/2000 | Kuroda et al. |
| 6,130,578 A | 10/2000 | Tang |
| 6,161,042 A | 12/2000 | Hartley et al. |
| 6,262,626 B1 | 7/2001 | Bakker et al. |
| 6,287,263 B1 | 9/2001 | Briskin |
| 6,360,123 B1 | 3/2002 | Kimchi et al. |
| 6,380,801 B1 * | 4/2002 | McCartney ............ H03F 3/3064 330/255 |
| 6,456,159 B1 | 9/2002 | Brewer |
| 6,463,328 B1 | 10/2002 | John |
| 6,483,355 B1 | 11/2002 | Lee et al. |
| 6,522,914 B1 | 2/2003 | Huvelle et al. |
| 6,539,261 B2 | 3/2003 | Dal Molin |
| 6,584,351 B1 | 6/2003 | Ekwall |
| 6,621,334 B2 | 9/2003 | Ausserlechner et al. |
| 6,625,436 B1 | 9/2003 | Tolson et al. |
| 6,639,460 B1 | 10/2003 | Baker |
| 6,667,760 B1 | 12/2003 | Limberg |
| 6,674,322 B2 | 1/2004 | Motz |
| 6,753,731 B2 | 6/2004 | Maki |
| 6,754,535 B2 | 6/2004 | Noren et al. |
| 6,810,285 B2 | 10/2004 | Pless et al. |
| 6,861,878 B2 | 3/2005 | Haruhana et al. |
| 6,876,842 B2 | 4/2005 | Davie |
| 6,904,321 B1 | 6/2005 | Bornzin et al. |
| 6,914,539 B2 | 7/2005 | Hoctor et al. |
| 6,946,890 B1 | 9/2005 | Lei et al. |
| 6,993,380 B1 | 1/2006 | Modarres |
| 7,006,872 B2 | 2/2006 | Gielen et al. |
| 7,010,347 B2 | 3/2006 | Schecter |
| 7,038,532 B1 | 5/2006 | Bocko et al. |
| 7,098,823 B2 | 8/2006 | O'Dowd et al. |
| 7,142,917 B2 | 11/2006 | Fukui |
| 7,146,208 B2 | 12/2006 | Holmstrom et al. |
| 7,146,218 B2 | 12/2006 | Esteller et al. |
| 7,170,338 B1 | 1/2007 | Tucker |
| 7,171,258 B2 | 1/2007 | Goode |
| 7,177,609 B1 | 2/2007 | Wong |
| 7,202,717 B2 | 4/2007 | Keaveney et al. |
| 7,233,198 B2 | 6/2007 | Niederkorn |
| 7,239,927 B2 | 7/2007 | Ganion |
| 7,253,685 B2 | 8/2007 | Chung |
| 7,262,654 B2 | 8/2007 | Kejariwal et al. |
| 7,295,061 B1 | 11/2007 | Dasgupta |
| 7,321,261 B2 * | 1/2008 | Felder ..................... H03F 1/26 327/124 |
| 7,336,123 B2 | 2/2008 | Yoshida et al. |
| 7,376,463 B2 | 5/2008 | Salo et al. |
| 7,391,257 B1 | 6/2008 | Denison et al. |
| 7,385,443 B1 | 7/2008 | Denison |
| 7,489,187 B2 | 2/2009 | Liu |
| 7,504,882 B2 | 3/2009 | Saito |
| 7,595,648 B2 | 9/2009 | Ungaretti et al. |
| 7,622,988 B2 | 11/2009 | Denison et al. |
| 7,671,672 B2 | 3/2010 | McConnell |
| 7,684,867 B2 | 3/2010 | Jaax et al. |
| 7,795,960 B2 * | 9/2010 | Lyden ..................... H03F 3/387 330/9 |
| 7,826,894 B2 | 11/2010 | Musallam et al. |
| 7,847,628 B2 | 12/2010 | Denison |
| 7,961,041 B2 | 6/2011 | Motz |
| 8,139,015 B2 | 3/2012 | Kawaguchi et al. |
| 8,265,769 B2 | 9/2012 | Denison |
| 8,330,537 B1 * | 12/2012 | Ghorpade ............ H03F 1/0277 330/136 |
| 8,354,881 B2 | 1/2013 | Denison |
| 8,928,406 B2 * | 1/2015 | Albinet ............... H03F 3/45636 330/253 |
| 9,294,049 B2 * | 3/2016 | Huijsing ................ H03F 1/56 |
| 2002/0038137 A1 | 3/2002 | Stein |
| 2002/0091332 A1 | 7/2002 | Bombardini |
| 2003/0146786 A1 | 8/2003 | Gulati et al. |
| 2004/0002635 A1 | 1/2004 | Hargrove et al. |
| 2004/0077967 A1 | 4/2004 | Jordan |
| 2004/0077987 A1 | 4/2004 | Jordan |
| 2004/0141558 A1 | 7/2004 | Plisch et al. |
| 2004/0158119 A1 | 8/2004 | Osorio et al. |
| 2004/0167418 A1 | 8/2004 | Nguyen et al. |

(56) References Cited

U.S. PATENT DOCUMENTS

| | | | |
|---|---|---|---|
| 2005/0007091 A1 | 1/2005 | Makeig et al. | |
| 2005/0081847 A1 | 4/2005 | Lee et al. | |
| 2005/0118968 A1 | 6/2005 | Cowley | |
| 2005/0182447 A1 | 8/2005 | Schecter | |
| 2005/0282517 A1 | 12/2005 | Cowley | |
| 2006/0055456 A1 | 3/2006 | Niederkorn | |
| 2006/0106275 A1 | 5/2006 | Raniere | |
| 2006/0116591 A1 | 6/2006 | Cooper | |
| 2006/0133550 A1 | 6/2006 | Bolton et al. | |
| 2006/0135877 A1 | 6/2006 | Giftakis et al. | |
| 2006/0139192 A1 | 6/2006 | Morrow et al. | |
| 2006/0139193 A1 | 6/2006 | Morrow et al. | |
| 2006/0173501 A1 | 8/2006 | Stickney et al. | |
| 2006/0184060 A1 | 8/2006 | Belalcazar et al. | |
| 2006/0212089 A1 | 9/2006 | Tass | |
| 2006/0241357 A1 | 10/2006 | Chirife | |
| 2006/0265022 A1 | 11/2006 | John et al. | |
| 2006/0281427 A1 | 12/2006 | Isaac et al. | |
| 2006/0293720 A1 | 12/2006 | DiLorenzo | |
| 2007/0010755 A1 | 1/2007 | Sarkela et al. | |
| 2007/0016095 A1 | 1/2007 | Low et al. | |
| 2007/0032737 A1 | 2/2007 | Causevic et al. | |
| 2007/0077907 A1 | 4/2007 | Rector | |
| 2007/0179534 A1 | 8/2007 | Firlik et al. | |
| 2007/0216477 A1 | 9/2007 | McConnell | |
| 2007/0249953 A1 | 10/2007 | Frei et al. | |
| 2008/0051839 A1 | 2/2008 | Libbus et al. | |
| 2008/0071314 A1 | 3/2008 | John | |
| 2008/0015659 A1 | 5/2008 | Zhang et al. | |
| 2008/0180278 A1 | 7/2008 | Denison | |
| 2008/0269630 A1 | 10/2008 | Denison et al. | |
| 2008/0269631 A1 | 10/2008 | Denison et al. | |
| 2008/0269841 A1 | 10/2008 | Grevious et al. | |
| 2009/0082691 A1 | 3/2009 | Denison et al. | |
| 2010/0033240 A1 | 2/2010 | Denison et al. | |
| 2010/0113964 A1 | 5/2010 | Wahlstrand et al. | |
| 2010/0114223 A1 | 5/2010 | Wahlstrand et al. | |
| 2010/0324442 A1 | 12/2010 | Blomqvist | |
| 2010/0327887 A1 | 12/2010 | Denison et al. | |
| 2011/0068861 A1 | 3/2011 | Denison | |

FOREIGN PATENT DOCUMENTS

| | | |
|---|---|---|
| EP | 0568197 A2 | 3/1993 |
| EP | 0789449 A2 | 8/1997 |
| GB | 1249395 | 10/1971 |
| GB | 2457683 A | 8/2009 |
| JP | 5615112 | 2/1981 |
| JP | 6224659 A | 8/1994 |
| JP | 7120207 A | 5/1995 |
| JP | 10504099 T | 4/1998 |
| JP | 2006279377 A | 10/2006 |
| JP | 4717841 B2 | 2/2007 |
| WO | 1997010747 A1 | 3/1997 |
| WO | 2002001711 A1 | 1/2002 |
| WO | 2002003087 A1 | 1/2002 |
| WO | 2006066098 A1 | 6/2006 |
| WO | 2006126186 A2 | 11/2006 |
| WO | 2008103078 A1 | 8/2008 |
| WO | 2008105692 A1 | 9/2008 |
| WO | 2009042172 A | 4/2009 |
| WO | 2009042313 A | 4/2009 |
| WO | 2012101467 A1 | 8/2012 |

OTHER PUBLICATIONS

"baseband." Authoritative Dictionary of IEEE Standard Terms (Seventh Edition). New York: IEEE 2000.

Abidi, "CMOS wireless transceivers: the new wave," IEEE Communications Magazine 37, Aug. 1999, pp. 119-124.

Andersen et al., "Recording Advances for Neural Prosthetics," in Engineering in Medicine and Biology Society, IEMBS 2004, 26th Annual International Conference of the IEEE, val. 7, Sep. 1-5, 2004, pp. 5352-5355.

Andersen et al., "Selecting the signals for a brain-machine interface," Current Opinion in Neurobiology, val. 14, Dec. 2004, pp. 720-726.

Araud, et al. "On the design of ultra-low noise amplifiers for ENG recording," DIE Universidad Católica (Montevideo, Uruguay), Sep. 6, 2007, 6 pp.

Avestruz et al., "A 5 µW/Channel Spectral Analysis IC for Chronic Bidirectional Brain-Machine Interfaces," IEEE Journal of Solid-Slate Circuits, val. 43, No. 12, Dec. 2008, 19 pp.

Bakker et al., "A CMOS nested chopper instrumentation amplifier with 100nV offset," IEEE Journal of Solid-Slate Circuits, Digest of Technical Papers, IEEE International, Dec. 2000, val. 35, No. 12, pp. 1877-1883.

Bakker, "High-Accuracy CMOS Smart Temperature Sensors," Thesis Delft University of Technology, Apr. 17, 2000, pp. 20, 21, 51 and 52.

Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997, 20 pp.

Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006, 2 pp.

Denison et al., "A 2.2µW 94nV/..JHz, Chopper-Stabilized Instrumentation Amplifier for EEG Detection in Chronic D Implants" JSSC, val. 42, No. 12, Feb. 13, 2007, pp. 2934-2945.

Denison et al., "A 2µW 100 nV/rtHz Chopper-Stabilized Instrumentation Amplifier for Chronic Measurement of Neural Field Potentials," Solid-slate circuits, IEEE Journal, val. 42, pp. 2934-2945, Dec. 2007.

Denison et al., "An 8~W heterodyning chopper amplifier for direct extraction of 2µVrms Neuronal Brain Biomarkers," ISSCC, paper 8.1, Feb. 5, 2008, 3 pp.

Denison et al., "An 8µW Heterodyning Chopper Amplifier for Direct Extraction of 2~Vrms Neuronal Biomarkers," Solid-Slate Circuits Conference, Feb. 5, 2008 Digest of Technical Papers, IEEE International, 3 pp.

Dzwonczyk et al., ""Myocardial Electrical Impedance Responds to Ischemia and Reperfusion in Humans,"" IEEE Transactions on Biomedical Engineering, IEEE Service Center, val. 51, No. 12, Dec. 2004, pp. 2206-2209.

Enz et al., "Circuit Techniques for Reducing the Effects of Opamp Imperfections," Proc. of the IEEE, vol. 84, No. 11, pp. 1584-1614, Nov. 1996.

Ge, et al., "A pseudo rail-to-rail chopper-stabilized instrumentation amplifier in 0.13 µm CMOS," Intel Corporation, Aug. 5, 2009, 4 pp.

Haddad et al., "An ultra-low-power dynamic translinear cardiac sense amplifier for pacemakers," Circuits and Systems, May 25-28, 2003, val. 5, pp. V37-V40.

Haddad et al., "Analog wavelet transform employing dynamic translinear circuits for cardiac signal characterization," Circuits and Systems, May 2003, val. 1, pp. 1-121-1-124.

Hadiashar et al., "A Chopper Stabilized CMOS Analog Multiplier with Ultra Low DC Offsets," Solid-State Circuits Conference, pp. 364-367, Sep. 2006.

Harrison et al. "A Low-Power Integrated Circuit for a Wireless 100-Eiectrode Neural Recording System." Solid state circuits. IEEE Journal of, val. 42, Jan. 2007, pp. 123-133.

Harrison et al., "A Low-Power Integrated Circuit for a Wireless 100-Electrode Neural Recording System," ISSCC Digest of Technical Papers 2006, paper 30.2, Feb. 2006.

Harrison et al., "A Low-Power Low-Noise CMOS Amplifier for Neural Recording Applications," IEEE J. of Solid-State Circuits, vol. 38, No. 6, pp. 958-965, Jun. 2003.

Harrison et al., "Local Field Potential Measurement with Low-Power Analog Integrated Circuit," Engineering in Medicine and Biology Society, 2004, IEMBS '04, 26th Annual International Conference of the IEEE, vol. 2, on pp. 4067-4070 vol. 6, Sep. 1-5, 2004.

Hosi, "Functional specialization within the dorsolateral prefrontal cortex: A review of anatomical and physiological studies of non-human primates," Neuroscience Research 54, 2006, pp. 73-84.

(56) References Cited

OTHER PUBLICATIONS

Jianping et al., "Study on Feature Extraction of the Sleep-Multigraph," Journal of Biomedical Engineering, Issue 5, vol. 22, pp. 906-909, Dec. 31, 2005.
Joshi, "Low-power low-noise analog signal conditioning chip with on-chip drivers for healthcare applications," Indian Institute of Technology, Bombay, India, Nov. 2012, pp. 828-837.
Krusienski et al., "A μ-Rhythm Matched Filter for Continuous Control of a Brain-Computer Interface," Biomedical Engineering, IEEE Transactions on, val. 54, Feb. 2007, pp. 273-280.
Kun et al., ""Algorithm for Tissue Ischemia Estimation Based on Electrical Impedance Spectroscopy,"" IEEE Transactions on Biomedical Engineering, IEEE Service Center, val. 50, No. 12, Dec. 2003, pp. 1352-1359.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, Jun. 18-20, 2008, pp. 76-77.
Liu, "Operational amplifiers," in: Demystifying Switched Capacitor Circuits (Demystifying Technology, vol. 1) May 11, 2006, pp. 15-26.
Makinaw et al., "A CMOS Temperature-to-frequency converter with an Inaccuracy of less than ±0.5 ° C. (3cr) from −40 ° C. to 105 ° C.," IEEE Journal of Solid State Circuits, val. 41, No. 12, Dec. 2006, pp. 2992-2997.
Makinwa, "Dynamic Offset Cancellation Techniques," Smart Sensor Systems '02, May 2002, 42 pp.
Martins et al., "A CMOS IC for Portable EEG Acquisition Systems," IEEE Transactions on Instrumentation and Measurement, vol. 47, No. 5, pp. 1191-1196, Oct. 1998.
Masui, ""A 0.6 V Supply CMOS Amplifier Using Noise Reduction Technique of Autozeroing and Chopper Stabilization,"" 21st Century COE Program, Hiroshima University, Proceedings of the Fifth Hiroshima International Workshop, Jan. 29-30, 2007, 15 pp.
Min et al., ""Electrical Impedance and Cardiac Monitoring-Technology, Potential and Applications,"" International Journal of Bioelectromagnetism, International Society for Bioelectromagnetism, vol. 5. No. 1, Jan. 2003, pp. 53-56.
Miranda et al., "A new electric conductance conversion method suitable for very low power applications," Polytechnic Institute of Leiria (Portugal); Centre for the Research and Technology of Agro-Environmental and Biological Sciences of UTAD (Portugal); INESC TEC and University of Trás-os-Montes e Alto Douro, Jan. 2014, pp. 379-385.
Moualla, et al., "Chopped Folded Cascode Bulk Driven OTA," Proceedings of the International Interdisciplinary Honeywell EMI 2005, May 26, 2005, pp. 185-189.
Ng et al., "A CMOS Analog Front-End IC for Portable EEG/ECG Monitoring Applications," IEEE Trans. on Circuits and Systems, vol. 52 No. 11, Nov. 2005, 13 pp.
Rajan et al., ""Offset cancellation and 1/f noise suppression scheme for chopper amplifiers,"" IEEE, 2000, pp. 68-71.
Rauscher, "Pratical Realization of an Analyzer Operating on the Heterodyne Principle," Chapter 4 (partial) of Fundamentals of Spectrum Analysis (Rhode & Schwarz, 2001), pp. 34-64.
Rudell, et al., Recent developments in high integration multi-standard CMOS transceivers for personal communication systems in Low Power Electronics and Design, pp. 149-154 (IEEE 1998).
Sal Thouse et al., "A practical micropower programmable bandpass filter for use in bionic ears," Solid-Slate Circuits, IEEE Journal, val. 38, No. 1, Jan. 2003, pp. 63-70.
Sanduleanu et al., "A Low Noise, Low Residual Offset, Chopped Amplifier for Mixed Level Applications," IEEE, 0-7803-5008-1/98, pp. 333-336, Sep. 1998.
Sarpeshkar et al., "An ultra-low-power programmable analog bionic ear processor," Biomedical Engineering, IEEE Transactions, val. 52, Apr. 2005, pp. 711-727.
Sarpeshkar et al., "Low power circuits for brain-machine interfaces," IEEE Transactions on Biomedical Circuits and Systems, Sep. 2008, val. 2, No. 3, pp. 173-183.
Sarpeshkar, "Borrowing from biology makes for low-power computing," IEEE Spectrum, pp. 24-29, May 2006.
Smart et al., "Automatic Detection of High Frequency Epileptiform Oscillations from Intracranial EEG Recordings of Patients with Neocortical Epilepsy," in Technical, Professional and Student Development Workshop, 2005 IEEE Region 5 and IEEE Denver Section, Apr. 7-8, 2005, pp. 53-58.
Watianapanitch et al., "An energy-efficient micropower neural recording amplifier," Biomedical Circuits and Systems, IEEE Transactions, val. 1, No. 2, Jun. 2007, pp. 136-147.
Wu et al., "A 1V 2.3mW Biomedical Signal Acquisition IC," ISSCC Digest of Technical Papers 2006, paper 2.7, Feb. 2006, 2 pp.
Yates, "An ultra-low power low noise chopper amplifier for wireless EEG," In $49^{th}$ IEEE International Midwest Symposium on Circuits and Systems, 2006, MWSCAS '06, vol. 2, pp. 449-452 (IEEE 2006).
Yazicioglu et al., "A 200μW Eight-Channel Acquisition ASIC for Ambulatory EEG Systems," Solid-Slate Circuits Conference, Feb. 5, 2008, 3 pp.
Yazicioglu et al., "A 60uW 60nV/rtHz Readout Front-End for Portable Biopotential Acquisition Systems," ISSCC Digest of Technical Papers 2006, paper 2.6, Feb. 2006, 2 pp.
Yiqian Ying, "Chopper Stabilized Amplifiers," Term Paper, Department of Electrical and Computer Engineering, University of Toronto, 17 pp., Nov. 12, 2001.

* cited by examiner

POWER-EFFICIENT CHOPPER AMPLIFIER

TECHNICAL FIELD

This disclosure relates to medical devices and, more particularly, to the monitoring of physiological signals with a medical device.

BACKGROUND

Medical devices may be used to deliver therapy to patients to treat a variety of symptoms or conditions. Examples of therapy include electrical stimulation therapy and drug delivery therapy. Examples of symptoms or conditions include chronic pain, tremor, akinesia, Parkinson's disease, epilepsy, dystonia, neuralgia, obsessive compulsive disorder (OCD), depression, sleep dysfunction, urinary or fecal incontinence, sexual dysfunction, obesity, or gastroparesis. Information relating to symptoms or conditions may be sensed by monitoring physiological signals, such as, e.g., electrocardiogram (ECG) signals, electromyogram (EMG) signals, electroencephalogram (EEG) signals, electrocorticogram (ECoG) signals, pressure signals, temperature signals, impedance signals, motion signals, and other types of signals.

In some cases, the physiological signals associated with a patient may be relatively low voltage signals that have information encoded at relatively low frequencies in the signal, such as, e.g., brain signals. Amplifying low frequency signals may present significant challenges in medical devices, particularly in the case of implantable medical devices where power resources may be limited.

SUMMARY

This disclosure describes techniques and circuitry for amplifying low frequency signals. A chopper amplifier may be used to amplify a signal with low frequency components to produce a resulting amplified signal with relatively low offset noise and relatively low 1/f noise (i.e., flicker noise or pink noise). In addition, random and/or thermal noise may be influenced by a transconductance of an amplifier. According to aspects of this disclosure, amplifier circuitry may include an amplification and transconductance unit configured to amplify a low frequency signal while also increasing transconductance and reducing power consumption. In some examples, the amplification and transconductance unit may include complementary transistors for amplifying and increasing a transconductance of a chopper modulated signal. In addition, in some examples, for differential applications, the amplification and transconductance unit may have complimentary pairs of transistors for amplifying and increasing the transconductance of the modulated signal.

In one example, an electrical circuit device for amplifying a physiological signal includes a modulation unit configured to receive an input signal, to modulate the input signal to produce a modulated signal, an amplification and transconductance unit configured to amplify an amplitude of the modulated signal and increase a transconductance of the modulated signal to produce a transconductance enhanced modulated and amplified signal, wherein the amplification and transconductance unit comprises at least a first complementary pair of transistors and a second complementary pair of transistors configured to receive the modulated signal and to amplify and increase the transconductance of the modulated signal, and a demodulation unit configured to receive the transconductance enhanced modulated and amplified signal and to demodulate the transconductance enhanced modulated and amplified signal to generate a chopper-stabilized amplified version of the input signal.

In another example, a method for amplifying a physiological signal includes modulating an input signal to produce a modulated signal, amplifying an amplitude and increasing a transconductance of the modulated signal, by a first complementary pair of transistors and a second complementary pair of transistors configured to receive the modulated signal, to produce a transconductance enhanced modulated and amplified signal, and demodulating the transconductance enhanced modulated and amplified signal to generate a chopper-stabilized amplified version of the input signal.

In another example, an apparatus for amplifying a physiological signal includes means for modulating an input signal to produce a modulated signal, means for receiving the modulated signal and amplifying an amplitude and an increasing a transconductance of the modulated signal to produce a transconductance enhanced modulated and amplified signal, wherein the means for receiving and amplifying comprises at least a first complementary pair of transistors and a second complementary pair of transistors configured to receive the modulated signal and to amplify and increase the transconductance of the modulated signal, and means for demodulating the transconductance enhanced modulated and amplified signal to generate a chopper-stabilized amplified version of the input signal.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

Like reference characters denote like elements throughout the figures and text.

DETAILED DESCRIPTION

This disclosure describes techniques and circuitry for amplifying low frequency signals. A chopper amplifier may be used to amplify a signal with low frequency components to produce a resulting amplified signal with relatively low offset noise and relatively low 1/f noise (i.e., flicker noise or pink noise). In addition, random and/or thermal noise may be influenced by a transconductance of an amplifier. According to aspects of this disclosure, amplifier circuitry may include an amplification and transconductance unit to amplify a low frequency signal while also increasing transconductance and reducing power consumption. In some examples, the amplification and transconductance unit may include complementary transistors for amplifying and increasing a transconductance of a chopper modulated signal. In addition, in some examples, for differential applications, the amplification and transconductance unit may have complimentary pairs of transistors for amplifying and increasing the transconductance of the modulated signal.

Sensing circuitry designed in accordance with the techniques of this disclosure may be used for sensing, monitoring, and analyzing a variety of signals including, e.g., electrocardiogram (ECG) signals, electromyogram (EMG) signals, electroencephalogram (EEG) signals, electrocorticogram (ECoG) signals, pressure signals, temperature signals, impedance signals, motion signals, and other types of signals. In addition, sensing circuitry designed in accordance with the techniques of this disclosure may be incorporated into a variety of implantable and non-implantable medical devices including, e.g., a pacemaker, defibrillator, or a neurostimulator, such as a neurostimulator configured to provide spinal cord stimulation, gastric stimulation, pelvic floor stimulation, peripheral nerve stimulation, or deep brain stimulation.

In some examples, the techniques of this disclosure may be used to sense, monitor, and analyze brain signals, such as, e.g., EEG signals, ECoG signals, and local field potentials (LFP's). Brain signals may include neurological biomarkers that are encoded as power fluctuations in particular frequency bands of the brain signal. For example, visual processing and motor planning may be correlated with power fluctuations in the alpha band (e.g., 5 to 15 Hz), and the symptoms of Parkinson's disease may be correlated with power fluctuations in the beta band (e.g., 15 to 35 Hz). Other target frequency bands of interest for brain signals may include the delta band (e.g., 1 Hz or lower), the theta band (e.g., 4 to 8 Hz), and the gamma band (e.g., 30-100 Hz).

A digital processor may be used to analyze power fluctuations of the brain signal in a specific frequency band. The power fluctuations in the brain signal may occur at relatively low frequencies and at a relatively low baseline power. The relatively low baseline power of the brain signal may make the signal difficult to analyze in a digital processor without amplification prior to digitization. The relatively low frequencies of interest in the brain signal may make the signal difficult to amplify without introducing noise (e.g., offset noise and 1/f noise) into the target frequency bands of interest, particularly in low power applications where the available power for the amplifier may be limited.

In addition, medical devices may be characterized by finite power resources that are required to last several months or years. To promote device longevity, sensing and therapy circuits are generally designed to consume relatively small levels of power. As an example, operation of a sensor circuit may require a supply current of less than 2.0 microamps or less than 1.0 microamps. In some examples, such a sensor circuit may consume supply current in a range of approximately 100 nanoamps to 1.0 microamps. Such a sensing circuit may generally be referred to as a micropower sensing circuit. Although medical devices are described for purposes of illustration, a micropower sensing circuit may be used in a variety of medical and non-medical test and measurement applications. In each case, the micropower sensing circuit may be required to draw low power, yet provide precise and accurate measurement.

Accordingly, an amplifier of a medical device may be designed to amplify an electrical signal between two electrodes in contact with body tissue while sustaining an acceptable signal to noise ratio (SNR) and also limiting the amount of power that is consumed. There may be two common noise sources associated with such an amplifier, including 1/f noise (and offset noise, as noted above) and random/thermal noise.

In some instances, 1/f noise may be removed using a chopper amplifier or a correlated double sampling (CDS) circuit. A chopper amplifier may be more power efficient than a CDS amplifier for some applications. In general, a chopper amplifier may be used to amplify a signal with low frequency components to produce a resulting amplified signal with relatively low offset and relatively low 1/f noise (i.e., flicker noise or pink noise). For example, a chopper amplifier is an example of a low power amplifier that may be used to amplify a brain signal to produce a resulting amplified signal with relatively low noise at low frequencies in the signal. A chopper amplifier may up-modulate a signal to be amplified based on a chopper frequency, amplify the up-modulated signal, and down-modulate the amplified signal based on the same chopper frequency to produce a chopper-stabilized amplified version of the input signal.

Thermal and random noise may be a function of a transconductance of amplifier input pairs. For example, increasing transconductance may result in a reduction in thermal noise. Thus, to achieve an efficient transconductance amplifier, transconductance may be increased for a given current consumption.

According to aspects of this disclosure, an amplifier having an amplification and transconductance unit may be configured to provide an accurate output at low frequency with relatively low power consumption. According to aspects of this disclosure, the amplification and transconductance unit may include one or more sets of transistors. The sets of transistors may include complementary NMOS and PMOS transistors. For example, for a single-ended (non-differential amplifier) amplification and transconductance unit may include complimentary NMOS and PMOS transistors. In another example, for a differential amplifier, amplification and transconductance unit may include one or more pairs of complimentary NMOS and PMOS transistors. In some examples, the techniques may be used to amplify a current drain of a sensing channel of a medical device, such as an implantable or external medical device for monitoring neural signals. The techniques may, in some instances, reduce the power consumption of such an amplifier by approximately 50% relative to an amplifier implementing chopper techniques alone.

Figure 1:
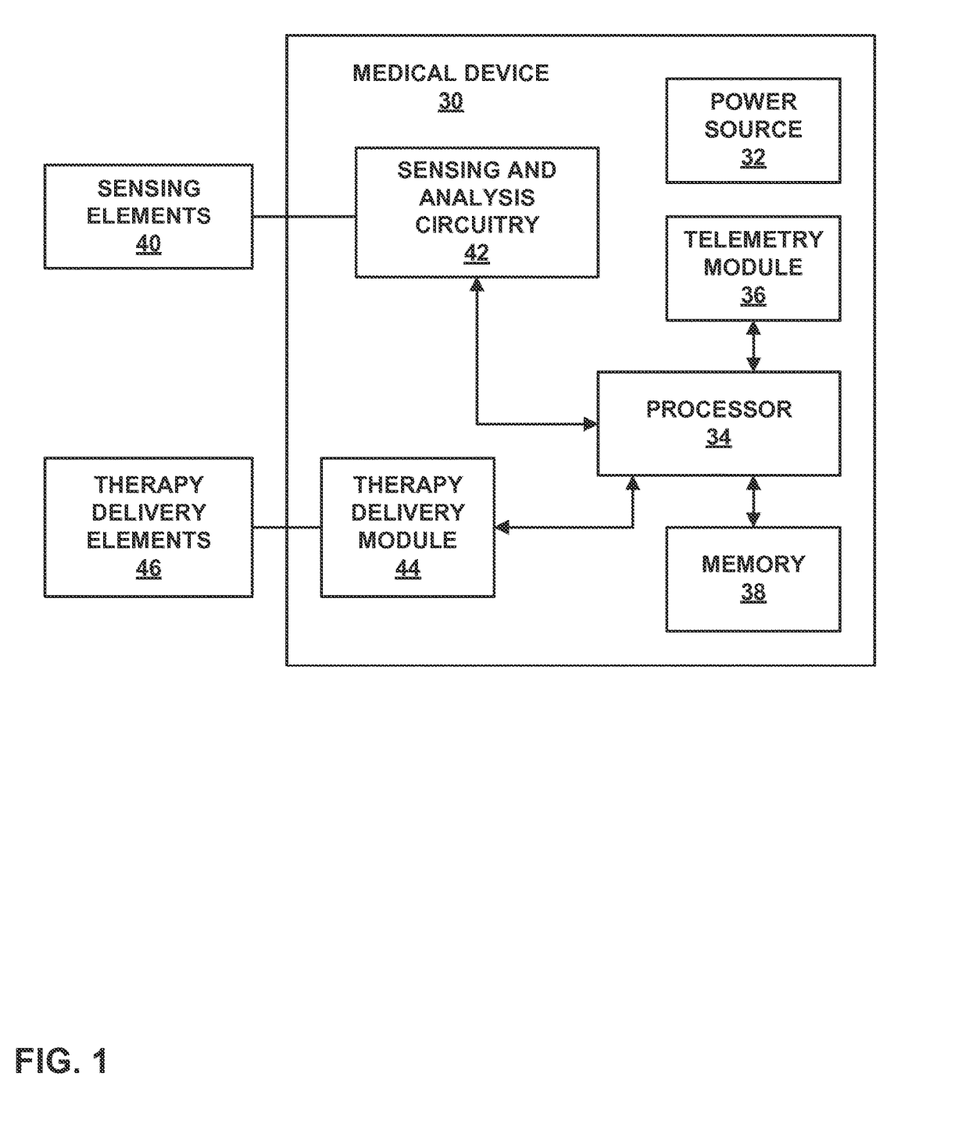
FIG. 1 is block diagram illustrating an example medical device in which the amplification techniques of this disclosure may be implemented.

FIG. 1 is block diagram illustrating an example medical device 30 that may perform the amplification techniques of this disclosure. In the example of FIG. 1, medical device 30 includes a power source 32, such as a rechargeable or nonrechargeable battery, a processor 34, a telemetry module 36, memory 38, sensing elements 40, sensing and analysis circuitry 42, a therapy delivery module 44, and therapy delivery elements 46. It should be understood that the components of medical device 30 are provided merely for purposes of example, and that medical device 30 may include more or fewer components than are shown in FIG. 1.

Power source 32 may provide operating power to components of medical device 30, such as processor 34, telemetry module 36, memory 38, sensing and analysis circuitry 42, and therapy delivery module 44. Power source 32 may take the form of a small, rechargeable or non-rechargeable battery, or an inductive power interface that receives inductively coupled energy. In the case of a rechargeable battery, power source 32 similarly may include an inductive power interface for transfer of recharge power.

Processor 34 may include one or more microprocessors, microcontrollers, digital signal processors (DSPs), application specific integrated circuits (ASICs), field programmable gate array (FPGAs), discrete logic circuitry, or a combination of such components. In general, processor 34 may control the functions of components of medical device 30, such as the functions of telemetry module 36 and/or therapy delivery module 44 based on data retrieved from memory 38 and/or signals received from sensing and analysis circuitry 42.

For example, processor 34 may control a telemetry module 36 to exchange information with an external programmer, such as a clinician programmer and/or patient programmer, by wireless, radio frequency (RF) telemetry. Processor 34 may control telemetry module 36 to communicate with the external programmer on a continuous basis, at periodic intervals, or upon request from the programmer. The programmer may, in turn, be connected to a computer that can program the device for algorithm and sensing adjustments, for issuing commands, for uplinking recorded loop data and for providing analysis. Alternatively or additionally, programmer may communicate directly with device 30 to, for example, perform one or more of the aforementioned functions. In addition, in some embodiments, telemetry module 36 may support wireless communication with one or more wireless sensors or sensing elements that sense physiological signals and transmit the signals to sensing and analysis circuitry 42 by wireless transmission.

Processor 34 may also communicate with memory 38. For example, memory 38 may store therapy instructions that are available to be selected by processor 34 in response to receiving a patient therapy trigger from sensing and analysis circuitry 42 and/or upon receiving a communication from programmer or another device. In addition, processor 34 may be configured to record diagnostic information, such as sensed signals, signal characteristics, or the like in memory 38 or another memory or storage device. Memory 38 may include any combination of volatile, non-volatile, removable, or solid state media, such as read-only memory (ROM), random access memory (RAM), electronically-erasable programmable ROM (EEPROM), flash memory, or the like.

Processor 34 may receive information via sensing elements 40 and sensing and analysis circuitry 42. In some examples, medical device 30 may comprise an implantable medical device capable of being implanted within the patient. In this case, sensing elements 40 may be positioned at a desired location within the patient to detect the physiological signal. In other examples, medical device 30 may comprise an external medical device with sensing elements 40 positioned at a desired location adjacent the patient to detect the physiological signal.

In general, sensing elements 40 provide a measurement of a physiological signal associated with the patient by translating the signal to an output voltage or current. Sensing elements 40 may include a variety of sensing elements, such as one or more pressure sensing elements, an accelerometer, an activity monitor, an impedance monitor, an electrical signal monitor or other monitor configured to monitor heart sounds, brain signals, and/or other physiological signals. Sensing elements 40 may include a set of electrodes for sensing electrical signals. The electrodes may be, for example, implantable electrodes deployed on a lead or external surface electrodes. Sensing elements 40 may be deployed at selected tissue sites or on selected surfaces of a human patient, such as within the brain, proximate the spinal cord, on the scalp, or elsewhere. As an example, scalp electrodes may be used to measure or record EEG signals. As another example, electrodes implanted at the surface of the cortex may be used to measure or record ECoG signals.

Sensing elements 40 may include one or more leads. A lead may carry one electrode or multiple electrodes, such as ring electrodes, segmented electrodes or electrodes arranged in a planar or non-planar array, e.g., on a paddle lead. Such leads may carry sense electrodes or a combination of sense and stimulation electrodes. In some cases, different leads may be dedicated to sensing and stimulation functions. If external, medical device 30 may be coupled to one or more leads carrying sense and/or stimulation electrodes via a percutaneous extension. As a further illustration, sensing elements 40 may be surface electrodes suitable for placement on scalp, face, chest, or elsewhere on a patient, in which case such electrodes may be coupled to sensing and analysis circuitry 42 via conductors within external leads. Sensing elements 40 may further comprise combinations of electrodes provided on one or more implantable leads and on or within a housing of medical device 30, or other electrode arrangements.

Sensing and analysis circuitry 42 may monitor the signals obtained from sensing elements 40. Sensing and analysis circuitry 42 may include suitable electrical interconnections to sensing elements 40 and other components, as necessary. Sensing and analysis circuitry 42 may output a trigger signal to processor 34 to control therapy and/or record diagnostic information. In such examples, processor 34 may receive the trigger signal and initiate delivery of therapy, stop delivery of therapy or adjust one or more therapy parameters specified in memory 38.

In some examples, sensing and analysis circuitry 42 may monitor and/or analyze physiological signals associated with a patient in selected frequency bands. The physiological signals may be relatively low frequency signals, and may have frequency bands of interest in a range of approximately 1 to 1000 Hertz (Hz) or, more particularly, in a range of approximately 1 to 500 Hz. For example, 1 Hz oscillations may be relevant for sleep state analysis, while fast ripples in a range of approximately 200 to 500 Hz or higher may be relevant for analysis of epilepsy. In general, frequencies in the selected frequency band are less than or equal to approximately 1000 Hz, more particularly less than or equal to approximately 500 Hz, and still more particularly less than or equal to approximately 100 Hz. For EEG signals, as an example, selected frequency bands may fall in the ranges of approximately 5 to 15 Hz (alpha band), 15 to 35 Hz (beta band), and 30 to 80 Hz (gamma band).

Characteristics of the signal in selected frequency bands may be useful in controlling therapy, such as electrical stimulation or drug delivery, either by initiation of delivery of therapy or adjustment of therapy parameters. Adjustment of therapy parameters may include adjustment of pulse amplitude, pulse rate, pulse width, electrode combination or the like for electrical stimulation, or adjustment of dosage, rate, frequency, lockout interval, or the like for drug delivery.

In some examples, sensing and analysis circuitry 42 may generate a signal indicative of a power of a target frequency band of a physiological signal and/or a signal indicative of power fluctuation of a target frequency band of a physiological signal. In such examples, processor 34 may trigger, stop, or adjust a delivery of therapy and/or trigger the recording of diagnostic information based on the signal indicative of the power of the target frequency band and/or the signal indicative of power fluctuation of the target frequency band. In some instances, sensing and analysis circuitry 42 may receive a measured physiological signal as an input signal, generate a chopper-stabilized amplified version of the input signal based on a chopper frequency, sample the chopper-stabilized amplified version of the physiological input signal at a sampling rate to generate a sampled signal, and analyze information contained in a target frequency band of the sampled signal.

According to aspects of this disclosure, as described in greater detail below, sensing and analysis circuitry 42 may include amplifier circuitry including an amplification and transconductance unit. The amplifier circuitry may be configured to provide an accurate output at low frequency with relatively low power consumption. A modulation unit of the amplifier circuitry may modulate a signal to be amplified from sensing elements 40 based on a chopper frequency. The amplification and transconductance unit may amplify the up-modulated signal and increase the transconductance of the up-modulated signal.

According to aspects of this disclosure, the increased transconductance (also referred to as enhanced transconductance) may be used to reduce random noise associated with sensing elements 40 and/or sensing and analysis circuitry 42. In some examples, the amplification and transconductance unit may include complementary pairs of transistors that are both driven by signals from the modulation unit, such as complementary pairs of NMOS and PMOS transistors. The transistor pairs may provide greater transconductance than a single NMOS pair or PMOS pair. The amplifier of sensing and analysis circuitry 42 may then down-modulate the amplified signal based on the same chopper frequency to produce a chopper-stabilized, amplified version of the input signal.

Processor 34 may output therapy instructions to therapy delivery module 44 to initiate, stop, or adjust delivery of therapy. Therapy delivery module 44 may be connected to therapy delivery elements 46, such as one or more electrodes deployed on a lead or drug delivery conduits, which may be positioned at a desired location relative to the patient to deliver therapy to the patient in response to the monitored physiological signal.

Again, medical device 30 may be an implantable device or an external device. Accordingly, therapy delivery elements 46 may be positioned at a desired location within the patient to deliver the therapy, such as electrical stimulation, drug delivery or internal audio or visual cueing. In other examples, therapy delivery elements 46 may be positioned at a desired location external to the patient to deliver the therapy, such as external audio, visual or tactile cueing via lights, displays, speakers, or the like.

In some cases, as described above, therapy delivery module 44 may include a stimulation generator or other stimulation circuitry that delivers electrical signals, e.g., pulses or substantially continuous signals, such as sinusoidal signals, to the patient via at least some of the electrodes that form therapy delivery elements 46, under the control of the therapy instructions received from processor 34. Processor 34 may control therapy delivery module 44 to deliver electrical stimulation with pulse voltage or current amplitudes, pulse widths and frequencies (i.e., pulse rates), and electrode combinations specified by the programs of the selected therapy instructions, e.g., as stored in memory 38. Processor 34 may also control therapy delivery module 44 to deliver each pulse, or a burst of pulses, according to a different program of the therapy instructions, such that multiple programs of stimulation are delivered in an interleaved or alternating basis. In some embodiments, processor 34 may control therapy delivery module 44 to deliver a substantially continuous stimulation waveform rather than pulsed stimulation.

In other cases, as described above, therapy delivery module 44 may include one or more fluid reservoirs and one or more pump units that pump fluid from the fluid reservoirs to the target site through the fluid delivery devices, such as one or more catheters, that form therapy delivery elements 46, under the control of the therapy instructions received from processor 34. For example, processor 34 may control which drugs are delivered and the dosage, rate and lockout interval of the drugs delivered. The fluid reservoirs may contain a drug or mixture of drugs. The fluid reservoirs may provide access for filling, e.g., by percutaneous injection of fluid via a self-sealing injection port. The fluid delivery devices may comprise, for example, fluid delivery conduits in the form of catheters that deliver, i.e., infuse or disperse, drugs from the fluid reservoirs to the same or different target sites.

In some cases, therapy delivery module 44 may include an audio signal generator, a visual signal generator, or a tactile stimulus (e.g., vibration) generator for cueing to disrupt akinesia or treat other conditions. Processor 34 may control therapy delivery module 44 to deliver audio, visual or tactile cueing with different parameters, such as amplitude, frequency, or the like, as specified by programs stored in memory 38.

As noted above, it should be understood that the components of medical device 30 are provided merely for purposes of example, and that medical device 30 may include more or fewer components shown in FIG. 1. In addition, it should be understood that certain components shown in medical device 30 of FIG. 1 may be highly integrated, but are illustrated separately for conceptual purposes. For example, in some instances, certain functions described with respect to sensing and analysis circuitry 42 may be carried out by processor 34, or vice versa.

Figure 2:
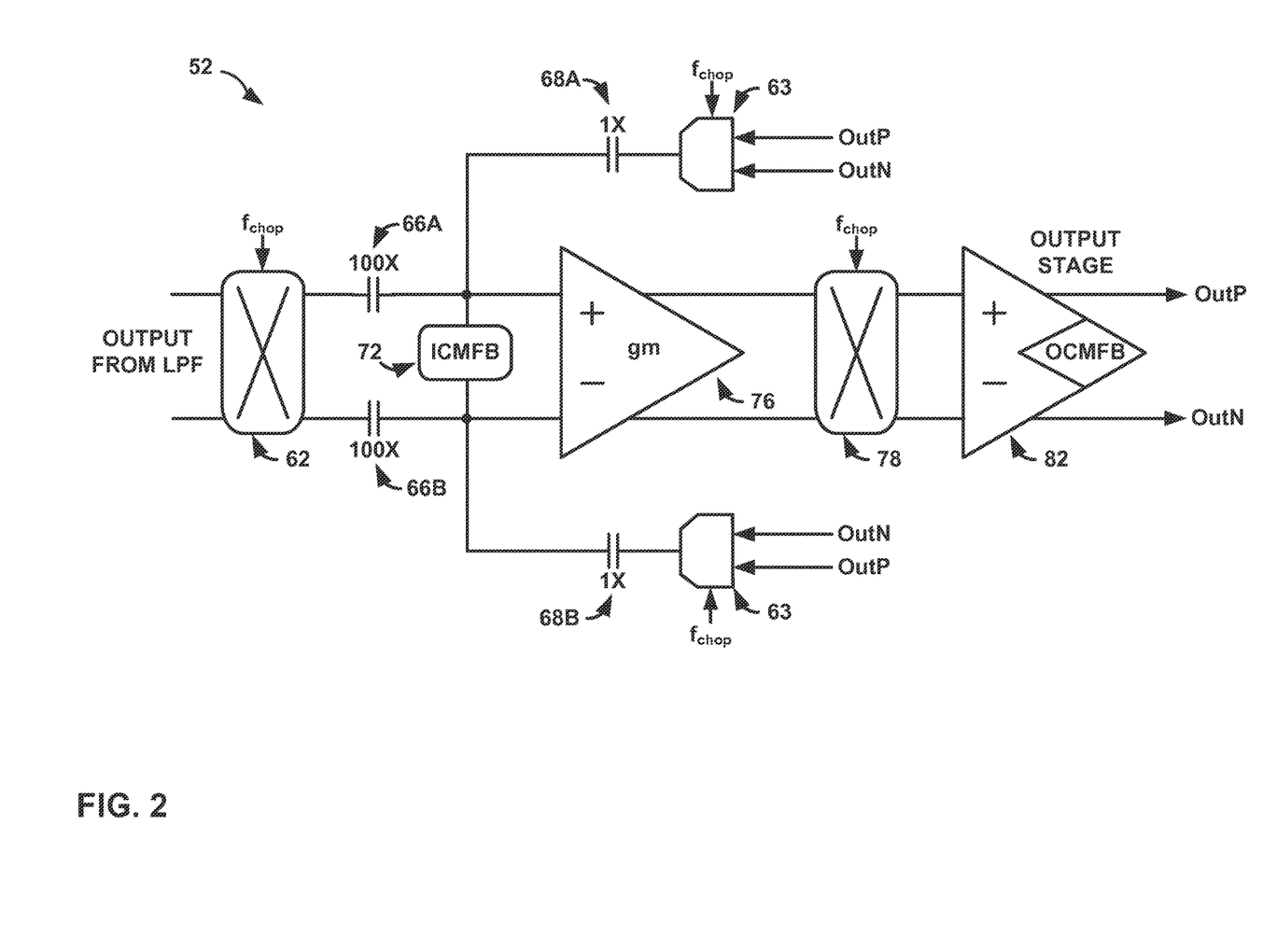
FIG. 2 is a circuit diagram illustrating example sensing and analysis circuitry that may be used to perform the amplification techniques of this disclosure.

FIG. 2 is a circuit diagram illustrating example amplifier circuitry 52 that may be used to perform the amplification techniques of this disclosure. In some examples, amplifier circuitry 52 may be incorporated in sensing and analysis circuitry 42 (FIG. 1). In the example shown in FIG. 2, amplifier circuitry 52 includes modulator 62 with feedback 63, first and second capacitors 66A and 66B, first and second feedback capacitors 68A and 68B, an input common mode feedback function block 72, a amplification and transconductance unit 76, a demodulator 78, and an output stage 82.

According to aspects of this disclosure, amplifier circuitry 52 may be configured to amplify an input signal received from one or more sensing elements, such as sensing elements 40 (FIG. 1). In some examples, the input signal may be a physiological signal received from one or more sensing elements (e.g., electrodes) that are attached to, proximate to, and/or implanted within a human being. As described in greater detail below, amplifier circuitry 52 may receive the input signal, modulate an amplitude of the input signal based on a chopper frequency to produce a modulated signal, and amplify an amplitude of the modulated signal to produce an amplified signal. Amplifier circuitry 52 may also increase a transconductance of the modulated signal to produce a transconductance enhanced modulated and amplified signal, and demodulate the transconductance enhanced modulated and amplified signal based on the chopper frequency to generate a chopper-stabilized amplified version of the input signal for output.

Modulator 62 may be configured to modulate an amplitude of an input signal based on a chopper frequency (i.e., $f_{chop}$) to produce a modulated signal. Modulating a signal based on a chopper frequency may refer to modulating the signal at the chopper frequency. In other words, modulator 62 may multiply a signal received by the respective modulator with the chopper frequency to produce an output signal (e.g., a modulated signal). Modulator 62 may also be referred to as a modulation unit and, while shown as a single component in the example of FIG. 2, may include a variety of components for modulating a signal. In some cases, modulator 62 may be constructed from one or more switches that are switched at the chopper frequency.

In some examples, modulator 62 and demodulator 78 may operate at the same chopper frequency. In other examples, modulator 62 and demodulator 78 may operate at different chopper frequencies. For example, in some instances, modulator 62 and demodulator 78 may operate using a selected frequency delta between the modulation frequency and demodulation frequencies. In an example for purposes of illustration, modulator 62 may operate at a particular chopper frequency $f_{chop}$ and demodulator 78 may operate at a second, difference chopper frequency $f_{chop+delta}$. In this example, amplifier circuitry 52 may produce an amplified, chopper-stabilized signal in a particular band of interest that may be defined based on the delta. Hence, amplifier circuitry 52 may comprise a frequency selective amplifier that may not require a bandpass filter at an output stage, such as output stage 82. Additional information regarding example chopper amplifiers may be disclosed, for example, in U.S. application Ser. No. 11/700,404, filed Jan. 31, 2007 and U.S. application Ser. No. 12/237,868, filed Sep. 25, 2008, the entire contents of which are incorporated by reference herein.

In some examples, modulator 62 may use a chopper frequency that is higher than a 1/f noise cutoff frequency (e.g., a 1/f noise corner). Selecting a chopper frequency that is higher than the 1/f noise corner may be effective for reducing 1/f noise and the DC offset of the signal. However, a higher chopper frequency typically results in lower input impedance, which may attenuate the signal being monitored/analyzed (OutP and OutN). In addition, a higher chopper frequency may make the amplifier more susceptible to common mode interference. A chopper frequency for physiological signals may be from approximately 2 kHz to 10 kHz. According to aspects of this disclosure, in some examples, modulator 62 may use a relatively high chopper frequency to minimize 1/f noise and DC offset. A transconductance portion, as described herein, may be used to offset the resulting lower input impedance and/or signal attenuation associated with the relatively high chopper frequency.

First and second capacitors 66A and 66B and first and second feedback capacitors 68A and 68B set a gain for amplification and transconductance unit 76. The example of FIG. 2 is shown as a differential amplifier. Feedback blocks 63 receive the chopper frequency (i.e., $f_{chop}$) and provide a feedback signal to first and second feedback capacitors 68A and 68B. A difference between the output signals of modulator 62 may be amplified using first and second capacitors 66A and 66B and first and second feedback capacitors 68A and 68B to set the gain for amplification and transconductance unit 76. A gain may be determined based on a ratio of first and second capacitors 66A and 66B and first and second feedback capacitors 68A and 68B. In the example, of FIG. 2, the capacitance values of capacitors 66A, 66B, 68A and 66B may be selected such that the gain of amplification and transconductance unit 76 is approximately 100 times the input signal (100×/1×). However, in other examples, first and second capacitors 66A and 66B and/or first and second feedback capacitors 68A and 68B may be selected to provide a different gain than that shown. Moreover, in other examples, components other than first and second capacitors 66A and 66B and/or first and second feedback capacitors 68A and 68B may be selected to control an amplification gain of amplifier circuitry 52.

Input common mode feedback function block 72 may represent circuitry configured to sense a common-mode voltage and compare the common mode voltage with a reference voltage. Input common mode feedback function block 72 may be responsible for feeding back a correcting common-mode signal to both nodes of amplification and transconductance unit 76.

Amplification and transconductance unit 76 may include circuitry for amplifying and increasing the transconductance of a received modulated signal. The increased transconductance may be used to reduce random and/or thermal noise associated with sensing elements, in instances in which amplifier circuitry is used to amplify physiological signals. According to aspects of this disclosure, and as described in greater detail with respect to FIGS. 3 and 4 below, amplification and transconductance unit 76 may include complementary pairs of transistors for amplifying and increasing the transconductance of the modulated signal. For example, according to aspects of this disclosure, modulator 62 may drive both complementary pairs of transistors of amplification and transconductance unit 76. In some instances, amplification and transconductance unit 76 may include at least two pairs of NMOS and PMOS transistors, which may provide a relatively greater increase in transconductance versus a single transistor pair. In some examples, NMOS and PMOS transistors are selected to have a sub-threshold region that maximizes the ratio of transconductance to bias current.

In some examples, demodulator 78 may be configured in a similar manner as modulator 62. Demodulator 78 may also be referred to as a demodulation unit and, while shown as a single component in the example of FIG. 2, may include a variety of components for demodulating a signal. For example, demodulator 78 may multiply a signal received by demodulator 78 with the chopper frequency to produce an output signal (e.g., a modulated signal). In some cases, demodulator 78 may be constructed from one or more switches that are switched at the chopper frequency. As noted above, in some examples, demodulator 78 may operate at the same frequency as modulator 62. In other examples, demodulator 78 may operate at a different frequency as modulator 62, e.g., to generate an output in a particular band of interest.

Output stage 82 may include a variety of components for filtering and/or conditioning an output from demodulator 78. For example, output stage 82 includes an output common mode function block ("OCMFB") that may sense a common-mode voltage of the output signal and correct the common-mode signal, e.g., by cancelling out the common mode portions of the signal. In some examples, output stage 82 may include a low-pass filter (LPF) (not shown in FIG. 2) for low-pass filtering the demodulated signal from demodulator 78. In some examples, the LPF may be an integrator or another type of low-pass filter that includes a pass band and a stop band. In some examples, output stage 82 may provide additional signal amplification. In some examples, amplifier circuitry 52 may be closed loop, such that the output from the LPF may be provided to modulator 62 ("output from LPF"). In addition, as described in greater detail with respect to FIG. 3, in some instances, output stage 82 may include one or more cascode devices to increase an output impedance of an output signal.

In operation, modulator 62 receives an input signal. As noted above, the input signal may be a physiological signal and may be a relatively low frequency signal. In some examples, the input signal may associated with a current drain of a transistor used in a sensing channel, such as a sensing channel associated with one or more of sensing elements 40. Modulator 62 may modulate the input signal based on a chopper frequency to produce a modulated signal.

First and second capacitors 66A and 66B and first and second feedback capacitors 68A and 68B may receive the modulated signal and may set the amplification gain for amplification and transconductance unit 76. Input common mode feedback function block (ICMFB) 72 may sense a common-mode voltage of the amplified signal and correct the common-mode signal, e.g., by cancelling out the common mode portions of the signal.

Amplification and transconductance unit 76 may receive the modulated signal from first and second capacitors 66A and 66B and first and second feedback capacitors 68A and 68B at respective first and second inputs of amplification and transconductance unit 76, and may amplify and increase the transconductance of the modulated signal to produce a transconductance enhanced modulated and amplified signal. As noted above, amplification and transconductance unit 76 may, in some instances, include complementary pairs of transistors for increasing the transconductance of the amplified signal.

Demodulator 78 may receive the transconductance enhanced modulated and amplified signal from amplification and transconductance unit 76 and may demodulate the transconductance enhanced modulated and amplified signal. In some examples, demodulator 78 may demodulate the received signal based on the chopper frequency (i.e., $f_{chop}$) to generate a chopper-stabilized amplified version of the input signal. In other examples, demodulator 78 may demodulate the received signal at a different chopper frequency, e.g., using a particular chopper frequency delta, to generate a chopper-stabilized amplified version of the input signal.

Output stage 82 may receive the chopper-stabilized amplified version of the input signal from demodulator 78, and may filter and/or condition the demodulated signal. For example, in some instances, output stage 82 may low pass filter the received signal to produce a filtered signal. The low pass filter may reduce or eliminate the chopper frequency (i.e., $f_{chop}$) aggressor in the output signal. In some examples, output stage 82 may also include a cascode portion to increase the output impedance of output stage 82. In some examples, output stage 82 may also provide additional signal amplification for the signal.

It should be understood that amplifier circuitry 52 is provided merely for purposes of example, and that the techniques of this disclosure for amplifying a signal may be carried out using more, fewer, or a different arrangement of components than those shown in FIG. 2, for example, as described below with respect to FIGS. 3 and 4.

Figure 3:
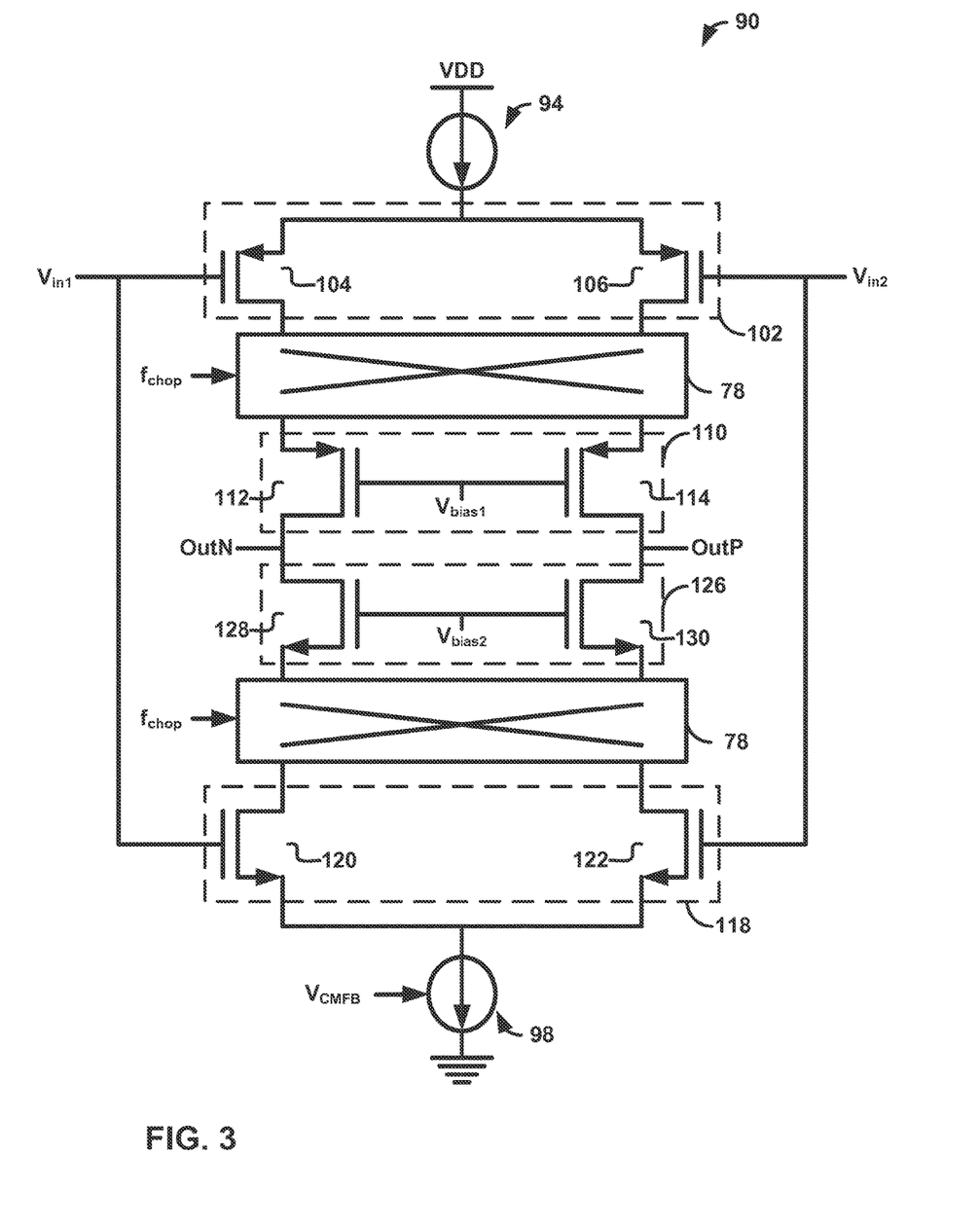
FIG. 3 is a circuit diagram illustrating example sensing and analysis circuitry that may be used to perform the amplification techniques of this disclosure.

FIG. 3 is a circuit diagram illustrating example amplifier circuitry 90 that may be used to perform the amplification techniques of this disclosure. In the example shown in FIG. 3, amplifier circuitry 90 includes PMOS and NMOS biasing voltage sources 94 and 98, respectively, a P-channel amplification and transconductance portion 102 having first PMOS transistor 104 and second PMOS transistor 106, a P-channel cascode portion 110 having first cascode PMOS transistor 112 and second cascode PMOS transistor 114, an N-channel amplification and transconductance portion 118 having first NMOS transistor 120 and second NMOS transistor 122, and an N-channel cascode portion 126 having first cascode NMOS transistor 128 and second cascode NMOS transistor 130. The example of FIG. 3 is shown having a differential configuration, with respective transistors of each transistor pair receiving respective differential inputs Vin1 and Vin2 (e.g., PMOS transistor 104 and NMOS transistor 120 being driven by Vin1, and PMOS transistor 106 and NMOS transistor 122 being driven by Vin2).

In some examples, at least a portion of amplifier circuitry 90 may be incorporated in amplifier circuitry 52 shown in the example of FIG. 2. For example, FIG. 3 includes demodulator 78. In addition, P-channel amplification and transconductance portion 102 and N-channel amplification and transconductance portion 118 may form at least a portion of amplification and transconductance unit 76 shown in FIG. 2. In addition, P-channel cascode portion 110 and N-channel cascode portion 126 may form at least a portion of output stage 82. It should be understood, however, that the components shown in FIG. 3 provide merely one example of components that may be included in amplifier circuitry 52, and that other examples may include more or fewer components than those shown in FIG. 3. For example, as described below with respect to the example of FIG. 4, amplification and transconductance unit 76 may include additional circuitry not shown in the example of FIG. 3.

In the example of FIG. 3, P-channel amplification and transconductance portion 102 includes a pair of PMOS transistors connected to differential input voltages Vin1 and Vin2 and demodulator 78. For example, first PMOS transistor 104 may have a source connected to PMOS biasing voltage 94, a gate connected to first input voltage Vin1 and a drain connected to demodulator 78. In addition, second PMOS transistor 106 may have a source connected to PMOS biasing voltage 94, a gate connected to second input voltage Vin2 and a drain connected to demodulator 78.

P-channel cascode portion 110 includes another pair of PMOS transistors connected to demodulator 78 and that contribute to differential output signals OutN (N-channel output) and OutP (P-channel output). For example, first cascode PMOS transistor 112 may have a source connected to demodulator 78, a gate connected to a first cascode biasing voltage $V_{bias1}$ and a drain connected to output signal OutN. In addition, second cascode PMOS transistor 114 may have a source connected to demodulator 78, a gate connected to first cascode biasing voltage $V_{bias1}$ and a drain connected to output signal OutP.

The N-channel circuitry of FIG. 3 may be complementary to the P-channel circuitry. For example, N-channel amplification and transconductance portion 118 includes a pair of NMOS transistors connected to differential input voltages Vin1 and Vin2 and demodulator 78. That is, first NMOS transistor 120 may have a source connected to NMOS biasing voltage 98, which may be adjusted based on common-mode feedback signal $V_{CMFB}$, a gate connected to first input voltage Vin1 and a drain connected to demodulator 78 (FIG. 2). In addition, second NMOS transistor 122 may have a source connected to NMOS biasing voltage 98, a gate connected to second input voltage Vin2 and a drain connected to demodulator 78.

N-channel cascode portion 126 includes another pair of NMOS transistors connected to demodulator 78 and that contribute to differential output signals OutN (N-channel output) and OutP (P-channel output). For example, first cascode NMOS transistor 128 may have a source connected to demodulator 78, a gate connected to a second cascode biasing voltage $V_{bias2}$ and a drain connected to output signal OutN. In addition, second cascode NMOS transistor 130 may have a source connected to demodulator 78, a gate connected to second cascode biasing voltage $V_{bias2}$ and a drain connected to output signal OutP.

In operation, amplifier circuitry 90 receives differential input voltages Vin1 and Vin2. In some examples, the differential input voltages Vin1 and Vin2 may correspond to low frequency signals (e.g., physiological signals) that have been modulated to a chopper frequency ($f_{chop}$) (e.g., via modulator 62 as described with respect to the example of FIG. 2). P-channel amplification and transconductance portion 102 may operate as a pull up network to amplify and increase the transconductance of the input signals Vin1 and Vin2. In some examples, the signals provided by P-channel amplification and transconductance portion 102 (for demodulation by demodulator 78) may be current signals having amplitudes that are proportional to the product of the input signal and the transconductance of P-channel amplification and transconductance portion 102.

Likewise, N-channel amplification and transconductance portion 118 may operate as a complementary pull down network to amplify and increase the transconductance of the input signals Vin1 and Vin2. In some examples, the signals provided by NMOS amplification and transconductance portion 118 (for demodulation by demodulator 78) may be current signals having amplitudes that are proportional to the product of the input signal and the transconductance of NMOS amplification and transconductance portion 118. In this way, P-channel amplification and transconductance portion 102 and N-channel amplification and transconductance portion 118 may operate to convert the input signals Vin1 and Vin2 into currents having relatively high transconductance. Increasing the transconductance of the input signals may help to reduce thermal or other random noise of the amplifier. For example, amplifier input noise power is typically inversely proportional to the transconductance of amplifier transistors.

According to aspects of this disclosure, the input signals Vin1 and Vin2 drive both transistor pairs (e.g., included in P-channel amplification and transconductance portion 102 and N-channel amplification and transconductance portion 118) in a sub-threshold region, thereby achieving a doubled transconductance versus a single NMOS transistor pair or a single PMOS transistor pair. As noted above, input signals Vin1 and Vin2 may be modulated input voltages generated by a chopper modulator (e.g., such as modulator 62 shown in FIG. 2), such that the modulator drives both sets of transistors, i.e., the transistors of P-channel amplification and transconductance portion 102 and N-channel amplification and transconductance portion 118.

In general, P-channel cascode portion 110 and N-channel cascode portion 126 may receive respective demodulated signals from demodulator 78 and may operate to increase the output impedance for output signals OutN and OutP. Cascode transistors may also improve the output impedance and open-loop gain of the amplifier. P-channel cascode portion 110 and N-channel cascode portion 126 may be biased by first cascode biasing voltage $V_{bias1}$ and second cascode biasing voltage $V_{bias2}$, respectively. Biasing voltage may ensure proper operation of the respective cascode portions. In some examples, first cascode biasing voltage $V_{bias1}$ and second cascode biasing voltage $V_{bias2}$ may provide constant biasing voltages.

In this way, the complementary pairs of transconductance transistors (e.g., a pair including first PMOS transistor 104/first NMOS transistor 120 and a pair including second PMOS transistor 106/second NMOS transistor 122) may achieve twice the transconductance relative to a single pair of transistors being driven by an input voltage. In addition, by driving both of the pairs of transconductance transistors using a signal at a chopper frequency (as noted above with respect to FIG. 2), amplifier circuitry 90 may achieve an output signal having relatively less noise with the same current versus the signal achieved driving either PMOS transistors or NMOS transistors alone. Accordingly, using such pairs of transistors in chopper amplifier circuitry may result in an approximately 50% reduction in current consumption versus a chopper amplifier having a single pair of transistors driven by a chopper modulated signal.

Figure 4:
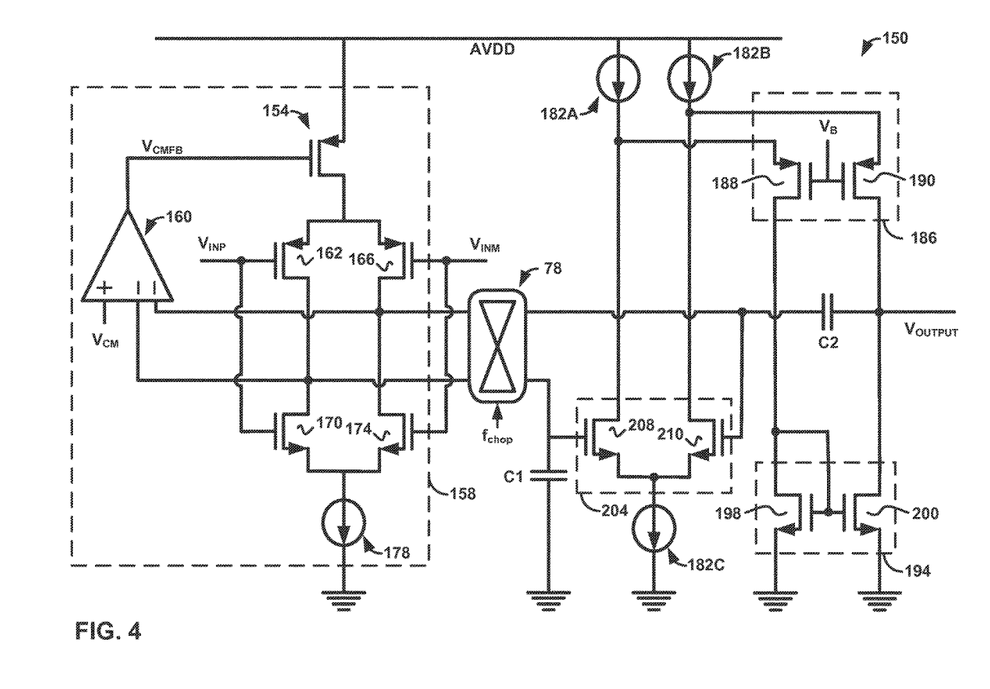
FIG. 4 is a circuit diagram illustrating example sensing and analysis circuitry that may be used to perform the amplification techniques of this disclosure.

FIG. 4 is a circuit diagram illustrating example amplifier circuitry 150 that may be used to perform the amplification techniques of this disclosure. In the example shown in FIG. 4, amplifier circuitry 150 includes demodulator 78 and an amplification and transconductance unit 158 that includes common-mode feedback circuit 160, common-mode transistor 154, first PMOS transistor 162, second PMOS transistor 166, first NMOS transistor 170, second NMOS transistor 174, transconductance biasing voltage source 178.

Amplifier circuitry 150 also includes biasing voltage sources 182A, 182B, and 182C (collectively, biasing voltages 182), a first filtering capacitor C1, a second filtering capacitor C2, a P-channel cascode transistor pair 186 having a first cascode PMOS transistor 188 and a second cascode PMOS transistor 190, a second cascode transistor pair 194 having a first cascode NMOS transistor 198 and a second cascode NMOS transistor 200, and a third transistor pair 204 including NMOS transistor 208 and NMOS transistor 210.

At least a portion of amplifier circuitry 150 may be incorporated in amplifier circuitry 52 shown in the example of FIG. 2. For example, FIG. 4 includes demodulator 78. In addition, amplification and transconductance unit 158 may form at least a portion of amplification and transconductance unit 76 shown in FIG. 2. In addition, biasing voltages 182, first filtering capacitor C1, second filtering capacitor C2, P-channel cascode transistor pair 186, second cascode transistor pair 194, and third transistor pair 204 may form at least a portion of output stage 82. It should be understood, however, that the components shown in FIG. 4 provide merely one example of components that may be included in amplifier circuitry 52, and that other examples may include more or fewer components than those shown in FIG. 4.

Common-mode feedback circuit 160 and common-mode transistor 154 define a common voltage for amplifier circuitry 150. Common-mode feedback circuit 160 has a common mode input $V_{CM}$ and inputs for transconductance portion 158, and an ouptut for common-mode compensated feedback voltage $V_{CMFB}$. The $V_{CM}$ input may be tied to a selected voltage level, which is the voltage level selected to be the common mode voltage for the signal provided to demodulator 78. $V_{CM}$ will be selected based on the swing of the signal that is provided to demodulator 78. The common-mode feedback voltage VCMFB is provided to a gate of common-mode transistor 154. In the example of FIG. 4, common-mode transistor 154 is a PMOS transistor having a source connected to analog supply voltage line (AVDD) and a drain connected to first transconductance PMOS transistor 162 and second transconductance PMOS transistor 166.

In general, amplification and transconductance unit 158 receives input voltages $V_{INP}$ and $V_{INM}$ and provides output signals to demodulator 78. In some examples, $V_{INP}$ and $V_{INM}$ may provide input voltages that have been modulated at a chopper frequency, such that a modulator (such as modulator 62 shown in FIG. 2) drives transistors 162, 166, 170, and 174. Sources of first PMOS transistor 162 and a second PMOS transistor 166 are connected to a drain of common-mode transistor 154. In addition, gates of first PMOS transistor 162 and a second PMOS transistor 166 are connected to input voltage $V_{INP}$ and input voltage $V_{INM}$, respectively. Drains of first PMOS transistor 162 and a second PMOS transistor 166 are connected to demodulator 78.

First NMOS transistor 170 and second NMOS transistor 174 have sources connected to transconductance biasing voltage 178. Gates of first NMOS transistor 170 and second NMOS transistor 174 are connected to input voltage $V_{INP}$ and input voltage $V_{INM}$, respectively. Drains of first NMOS transistor 170 and second NMOS transistor 174 are connected to demodulator 78.

Biasing voltages 182A, 182B, and 182C (collectively, biasing voltages 182) may provide biasing voltages for the remaining transistors of amplifier circuitry 150. For example, biasing voltage 182A is connected to a source of first cascode PMOS transistor 188 and a drain of NMOS transistor 208. Biasing voltage 182B is connected to a source of second cascode PMOS transistor 190 and a drain of NMOS transistor 210. Biasing voltage 182C is connected to sources of NMOS transistor 208 and NMOS transistor 210.

In the example of FIG. 4, first filtering capacitor C1 is connected, at one node, to demodulator 78 and a gate of NMOS capacitor 208. An opposite node of capacitor C1 is coupled to ground. Second filtering capacitor C2 is connected to demodulator 78 and a gate of NMOS transistor 210, at one node, with an opposite node connected to drains of PMOS transistor 190, NMOS transistor 200, and $V_{OUTPUT}$.

A source of first cascode PMOS transistor 188 is connected to biasing voltage 182A, while a gate of first cascode PMOS transistor 188 is connected to another biasing voltage $V_B$ and a drain of first cascode PMOS transistor 188 is connected to second cascode pair 194. A source of second cascode PMOS transistor 190 is connected to biasing voltage 182B, while a gate of second cascode PMOS transistor 190 is connected to another biasing voltage $V_B$ and a drain of second cascode PMOS transistor 190 is connected to second cascode NMOS transistor 200.

First cascode NMOS transistor 198 has a drain and gate connected to the drain of first cascode PMOS transistor 188 and a source connected to ground. Second cascode NMOS transistor 200 has a drain connected to the drain of second cascode PMOS transistor 190 and output $V_{OUTPUT}$, a gate connected to the drain of first cascode PMOS transistor 188, and a source connected to ground.

Third transistor pair 204 including NMOS transistor 208 and NMOS transistor 210 are also connected to demodulator 78. For example, NMOS transistor 208 has a source connected to biasing voltage 182C, a gate connected to demodulator 78 and first filtering capacitor C1, and a drain connected to biasing voltage 182A and the source of first cascode PMOS transistor 188. NMOS transistor 210 has a source connected to biasing voltage 182C, a gate connected to demodulator 78, and a drain connected to biasing voltage 182B and the source of second cascode PMOS transistor 190.

In operation, common-mode feedback circuit 160 and common-mode transistor 154 define a common voltage for amplifier circuitry 150. According to aspects of this disclosure, common-mode feedback circuit 160 accounts for common-mode signals introduced by the pairs of complementary transistors 162, 166, 170, and 174 of amplification and transconductance unit 158. As noted above, common-mode feedback circuit 160 generates common-mode feedback voltage $V_{CMFB}$, which is provided to the gate of common-mode transistor 154.

Amplification and transconductance unit 158 may amplify and increase the transconductance of a chopper modulated signal prior to demodulation by demodulator 78. For example, as noted above, transistors 162, 166, 170, and 174 may receive input voltages $V_{INP}$ and $V_{INM}$ and may amplify and increase the transconductance of such signals. In instances in which amplifier circuitry 150 is included in an external or implantable medical device, $V_{INP}$ and $V_{INM}$ may be modulated (e.g., at a chopper frequency $f_{chop}$) physiological signals (e.g., such as signals from an EEG, an ECoG, an LFP, or a single cell action sensor). As noted above with respect to FIG. 3, amplification and transconductance unit 158 may achieve twice the transconductance relative to a single pair of transistors.

As described above with respect to FIGS. 2 and 3, demodulator 78 demodulates the signals received from amplification and transconductance unit 158. Again, demodulator 78 may operate at the same chopper frequency or a different chopper frequency as a modulator, such as modulator 62. As noted above, chopper stabilization techniques may be used to reduce imperfections such as 1/f noise and DC offset associated with amplifying typically weak (e.g., in some instances, passive) signals. After signals are modulated to a relatively higher frequency where there is less 1/f noise and the signals are amplified, demodulator 78 demodulates the signal back to base-band or near base-band (and modulates the noise to be removed).

First filtering capacitor C1 and second filtering capacitor C2 may serve as compensation capacitors to promote stability of the amplifier. The first filtering capacitor C1 and second filtering capacitor C2 may also provide filtering for signals from demodulator 78. For example, first filtering capacitor C1 and second filtering capacitor C2 filter the demodulated signal from demodulator 78 to clean up the output signal and remove modulated noise and/or other artifacts. First filtering capacitor C1 and second filtering capacitor C2 may act as low pass filters to filter the demodulated signal from demodulator 78.

First cascode transistor pair 186 and second cascode pair 194 may increase the output impedance for output signal $V_{OUTPUT}$. Third transistor pair 204 including NMOS transistor 208 and NMOS transistor 210 may be used as input transistors for a second stage of the amplifier to provide additional signal gain. For example, third transistor pair 204 may provide a second stage for amplifier circuitry 150 to increase the signal gain at $V_{OUTPUT}$.

Figure 5:
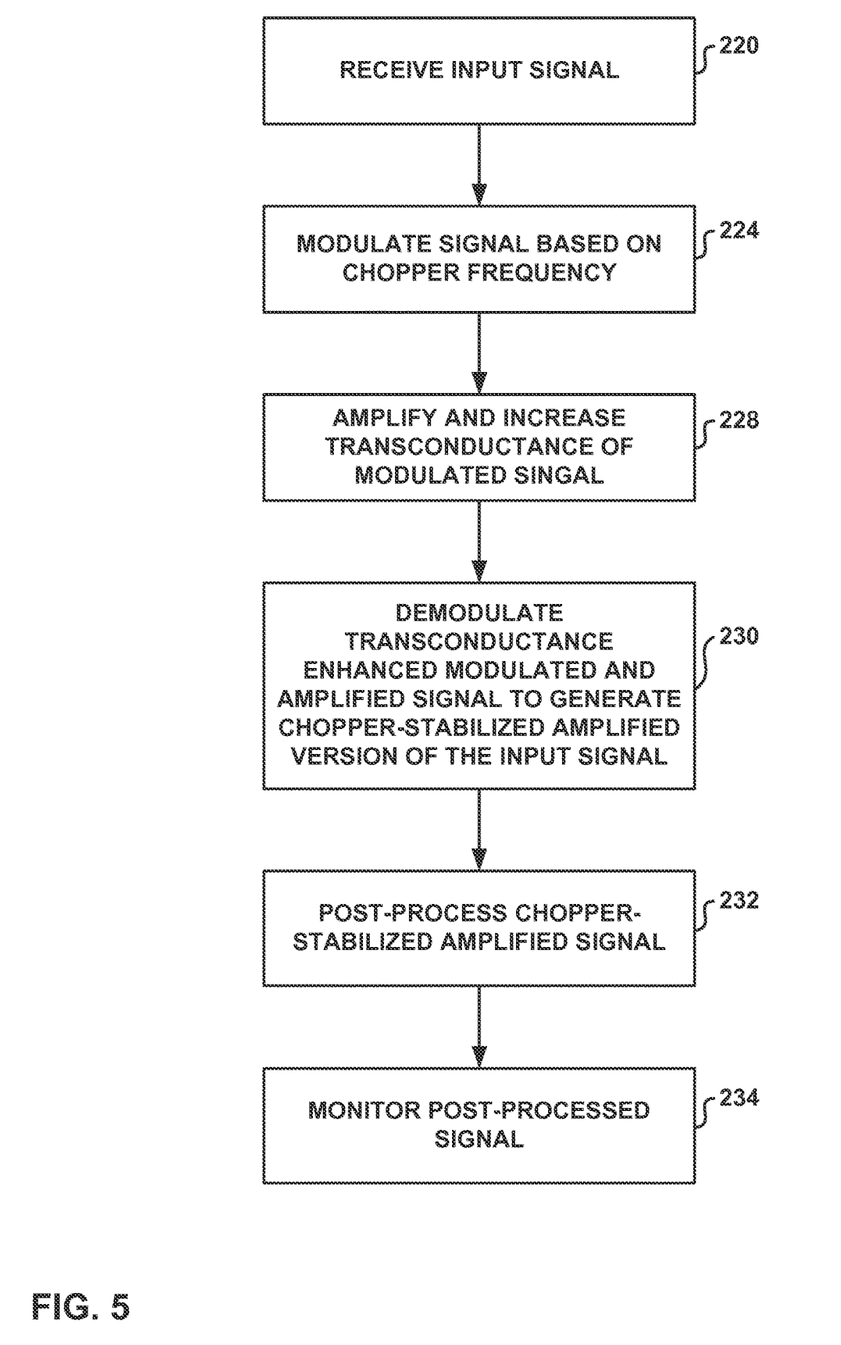
FIG. 5 is a flow diagram illustrating an example technique for amplification according to this disclosure.

FIG. 5 is a flow diagram illustrating an example technique for controlling spectral aggressors according to this disclosure. While described with respect to amplifier circuitry 52 (FIG. 2), it should be understood that the techniques described with respect to FIG. 5 may be performed using a variety of other circuitry having more, fewer, or an alternative arrangement of components than that shown in FIG. 2, e.g., such as the examples shown in FIGS. 3 and 4, or a variety of other circuit devices having alternative components.

Amplifier circuitry 52 receives an input signal (220). As noted above, in some examples, the signal may be one or more physiological signals (e.g., such as signals from an EEG, an ECoG, an LFP, or a single cell action sensor). In some examples, the signals may be passive signals received, e.g., from sensing elements 40 (FIG. 1). Modulator 62 of amplifier circuitry 52 may modulate the input signal based on a chopper frequency (i.e., $f_{chop}$) (224).

According to aspects of this disclosure, amplification and transconductance unit portion 76 may amplify and increase the transconductance of, the modulated signal (228). In some examples, the increased transconductance may be achieved via complementary pairs of transistors. In some examples, as described above with respect to FIG. 2, a number of capacitors may be used to set a gain for amplification of the modulated signal. However, the techniques of this disclosure are not limited in this way, and a variety of other components may also be incorporated in amplifier circuitry performing the techniques of this disclosure.

Demodulator 78 of amplifier circuitry 52 may receive the transconductance enhanced modulated and amplified signal and may demodulate the transconductance enhanced modulated and amplified signal based on the chopper frequency (i.e., $f_{chop}$) to generate a chopper-stabilized amplified version of the input signal (230). For example, demodulator 78 may modulate amplifier offset and low frequency noise (1/f noise) to remove the amplifier offset and noise from the signal band to the first order. Demodulator 78 may also return the transconductance enhanced modulated and amplified signal back to base-band.

In some examples, amplifier circuitry 52 may also perform post-processing of the chopper-stabilized signal (232). For example, as described with respect to FIG. 2 above, output stage 82 may include a low pass filter for removing the amplifier offset and noise from the demodulated signal. According to some aspects of this disclosure, as described with respect to FIGS. 3 and 4 above, a cascode stage may be included to increase the output impedance of the chopper-stabilized signal. In still other examples, as described with respect to FIG. 4 above, one or more additional amplification stages may be included to further amplify the chopper-stabilized signal. Other post-processing not specifically described herein may also be performed.

The post-processed signal may then be monitored (234). In some examples, amplifier circuitry 52 may include a filter for filtering a particular band of interest. Additionally or alternatively, modulator 62 and demodulator 78 may operate using a delta between chopper frequencies, which may generate an output in a particular band of interest. In any case, as noted above, the techniques described herein may be used for sensing, monitoring, and analyzing a variety of signals including, e.g., electrocardiogram (ECG) signals, electromyogram (EMG) signals, electroencephalogram (EEG) signals, electrocorticogram (ECoG) signals, pressure signals, temperature signals, impedance signals, motion signals, and other types of signals.

Various techniques described in this disclosure may be implemented in hardware, software, firmware or any combination thereof. For example, various aspects of the techniques may be implemented within or in conjunction with one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to cause a processor to perform or support one or more aspects of the functionality described in this disclosure.

Various aspects and examples have been described. However, modifications can be made to the structure or techniques of this disclosure without departing from the scope of the following claims.

What is claimed is:

1. An electrical circuit device for amplifying a physiological signal, the device comprising:
   a modulation unit configured to receive an input signal generated based on the physiological signal, and to modulate the input signal to produce a modulated signal;
   an amplification and transconductance unit configured to amplify an amplitude of the modulated signal and increase a transconductance of the modulated signal to produce a transconductance enhanced modulated and amplified signal, wherein the amplification and transconductance unit comprises at least a first complementary pair of transistors and a second complementary pair of transistors configured to receive the modulated signal and to amplify and increase the transconductance of the modulated signal; and
   a demodulation unit configured to receive the transconductance enhanced modulated and amplified signal and to demodulate the transconductance enhanced modulated and amplified signal to generate a chopper-stabilized amplified version of the input signal,
   wherein a gate of a first PMOS transistor of the first complementary pair of transistors is connected to the modulation unit to receive a first differential voltage signal from the modulation unit, and a drain of the first PMOS transistor of the first complementary pair of transistors is connected to the demodulation unit,
   wherein a gate of a first NMOS transistor of the first complementary pair of transistors is connected to the modulation unit to receive the first differential voltage signal from the modulation unit, and a drain of the first NMOS transistor of the first complementary pair of transistors is connected to the demodulation unit, wherein:
      the drain of the first PMOS transistor is commonly connected to the drain of the first NMOS transistor, and
      the voltage at the drain of the first PMOS transistor is substantially equal to the voltage at the drain of the first NMOS transistor throughout a voltage range at the drain of the first PMOS transistor,
   wherein a gate of a second PMOS transistor of the second complementary pair of transistors is connected to the modulation unit to receive a second differential voltage signal from the modulation unit, and a drain of the second PMOS transistor of the second complementary pair of transistors is connected to the demodulation unit, and
   wherein a gate of the second NMOS transistor of the second complementary pair of transistors is connected to the modulation unit to receive the second differential voltage signal from the modulation unit, and a drain of the second NMOS transistor of the second complementary pair of transistors is connected to the demodulation unit the demodulation unit, wherein:
      the drain of the second PMOS transistor is commonly connected to the drain of the second NMOS transistor, and the voltage at the drain of the second PMOS transistor is substantially equal to the voltage at the drain of the second NMOS transistor throughout a voltage range at the drain of the second PMOS transistor.

2. The electrical circuit device of claim 1, further comprising a cascode portion configured to receive the chopper-stabilized amplified version of the input signal and to increase an impedance of the chopper-stabilized amplified version of the input signal.

3. The electrical circuit device of claim 2, wherein the amplification and transconductance unit includes a PMOS circuit portion and an NMOS circuit portion, and wherein the cascode portion comprises a PMOS cascode portion and a NMOS cascode portion, wherein the PMOS cascode portion is connected to the PMOS circuit portion and the NMOS cascode portion is connected to the NMOS circuit portion.

4. The electrical circuit device of claim 1, further comprising a low pass filter unit configured to low pass filter the chopper-stabilized amplified version of the input signal.

5. The electrical circuit device of claim 1, wherein the low pass filter comprises one or more capacitors.

6. The electrical circuit device of claim 1, wherein the amplification and transconductance unit form at least a portion of a first amplifier stage, the electrical circuit device further comprising a second amplifier stage configured to receive the amplified signal from a chopper circuit portion of the first amplifier stage and to increase a gain of the chopper-stabilized amplified version of the input signal.

7. The electrical circuit device of claim 1, wherein the modulation unit is configured to modulate the input signal based on a first chopper frequency, and wherein the demodulation unit is configured to demodulate the transconductance enhanced modulated and amplified signal based on a second chopper frequency, wherein the first chopper frequency is equal to the second chopper frequency.

8. The electrical circuit device of claim 1, wherein the modulation unit is configured to modulate the input signal based on a first chopper frequency, and wherein the demodulation unit is configured to demodulate the transconductance enhanced modulated and amplified signal based on a second chopper frequency, wherein the first chopper frequency is different than the second chopper frequency.

9. The electrical circuit device of claim 1, wherein the physiological signal is a brain signal comprising at least one of an electroencephalogram (EEG) signal, an electrocorticogram (ECoG) signal, a local field potential (LFP) signal, or a single cell action potential signal.

10. The electrical circuit device of claim 1, further comprising a processor configured to monitor the chopper-stabilized amplified version of the input signal.

11. The electrical circuit device of claim 10, wherein the device comprises an implantable medical device.

12. A method for amplifying a physiological signal, the method comprising:
modulating, with a modulation unit, an input signal generated based on the physiological signal, and to produce a modulated signal;
amplifying an amplitude and increasing a transconductance of the modulated signal with an amplification and transconductance unit comprising a first complementary pair of transistors and a second complementary pair of transistors configured to receive the modulated signal, to produce a transconductance enhanced modulated and amplified signal; and
demodulating, with a demodulation unit, the transconductance enhanced modulated and amplified signal to generate a chopper-stabilized amplified version of the input signal,
wherein a gate of a first PMOS transistor of the first complementary pair of transistors is connected to the modulation unit to receive a first differential voltage signal from the modulation unit, and a drain of the first PMOS transistor of the first complementary pair of transistors is connected to the demodulation unit,
wherein a gate of a first NMOS transistor of the first complementary pair of transistors is connected to the modulation unit to receive the first differential voltage signal from the modulation unit, and a drain of the first NMOS transistor of the first complementary pair of transistors is connected to the demodulation unit, wherein:
the drain of the first PMOS transistor is commonly connected to the drain of the first NMOS transistor, and
the voltage at the drain of the first PMOS transistor is substantially equal to the voltage at the drain of the first NMOS transistor throughout a voltage range at the drain of the first PMOS transistor,
wherein a gate of a second PMOS transistor of the second complementary pair of transistors is connected to the modulation unit to receive a second differential voltage signal from the modulation unit, and a drain of the second PMOS transistor of the second complementary pair of transistors is connected to the demodulation unit, and
wherein a gate of the second NMOS transistor of the second complementary pair of transistors is connected to the modulation unit to receive the second differential voltage signal from the modulation unit, and a drain of the second NMOS transistor of the second complementary pair of transistors is connected to the demodulation unit, wherein:
the drain of the second PMOS transistor is commonly connected to the drain of the second NMOS transistor, and
the voltage at the drain of the second PMOS transistor is substantially equal to the voltage at the drain of the second NMOS transistor throughout a voltage range at the drain of the second PMOS transistor.

13. The method of claim 12, further comprising receiving the chopper-stabilized amplified version of the input signal and increasing an impedance of the chopper-stabilized amplified version of the input signal.

14. The method of claim 12, further comprising low pass filtering the chopper-stabilized amplified version of the input signal.

15. The method of claim 12, further comprising further amplifying the chopper-stabilized amplified version of the input signal.

16. The method of claim 12, wherein the physiological signal is a brain signal comprising at least one of an electroencephalogram (EEG) signal, an electrocorticogram (ECoG) signal, a local field potential (LFP) signal, or a single cell action potential signal.

17. The method of claim 12, further comprising monitoring the chopper-stabilized amplified version of the input signal.

18. The method of claim 12, wherein the modulating the input signal comprises modulating the input signal based on a first chopper frequency, and wherein demodulating the transconductance enhanced modulated and amplified signal comprises demodulating based on a second chopper frequency, wherein the first chopper frequency is equal to the second chopper frequency.

19. The method of claim 12, wherein the modulating the input signal comprises modulating the input signal based on a first chopper frequency, and wherein demodulating the transconductance enhanced modulated and amplified signal comprises demodulating based on a second chopper frequency, wherein the first chopper frequency is different than the second chopper frequency.

20. An apparatus for amplifying a physiological signal, the apparatus comprising:
- means for modulating an input signal generated based on the physiological signal, and to produce a modulated signal;
- means for receiving the modulated signal and amplifying an amplitude and an increasing a transconductance of the modulated signal to produce a transconductance enhanced modulated and amplified signal, wherein the means for receiving and amplifying comprises at least a first complementary pair of transistors and a second complementary pair of transistors configured to receive the modulated signal and to amplify and increase the transconductance of the modulated signal; and
- means for demodulating the transconductance enhanced modulated and amplified signal to generate a chopper-stabilized amplified version of the input signal,
- wherein a gate of a first PMOS transistor of the first complementary pair of transistors is connected to the means for modulating to receive a first differential voltage signal from the means for modulating, and a drain of the first PMOS transistor of the first complementary pair of transistors is connected to the means for demodulating,
- wherein a gate of a first NMOS transistor of the first complementary pair of transistors is connected to the means for modulating to receive the first differential voltage signal from the means for modulating, and a drain of the first NMOS transistor of the first complementary pair of transistors is connected to the means for demodulating, wherein:
  - the drain of the first PMOS transistor is commonly connected to the drain of the first NMOS transistor, and
  - the voltage at the drain of the first PMOS transistor is substantially equal to the voltage at the drain of the first NMOS transistor throughout a voltage range at the drain of the first PMOS transistor,
- wherein a gate of a second PMOS transistor of the second complementary pair of transistors is connected to the means for modulating to receive a second differential voltage signal from the means for modulating, and a drain of the second PMOS transistor of the second complementary pair of transistors is connected to the means for demodulating, and
- wherein a gate of the second NMOS transistor of the second complementary pair of transistors is connected to the means for modulating to receive the second differential voltage signal from the means for modulating, and a drain of the second NMOS transistor of the second complementary pair of transistors is connected to the means for demodulating, wherein:
  - the drain of the second PMOS transistor is commonly connected to the drain of the second NMOS transistor, and
  - the voltage at the drain of the second PMOS transistor is substantially equal to the voltage at the drain of the second NMOS transistor throughout a voltage range at the drain of the second PMOS transistor.

* * * * *